(12) United States Patent
Yang et al.

(10) Patent No.: US 6,372,848 B1
(45) Date of Patent: Apr. 16, 2002

(54) BLEND OF ETHYLENE AND α-OLEFIN COPOLYMERS OBTAINED USING A METALLOCENE CATALYST FOR FABRICATING MEDICAL FILMS AND TUBINGS

(75) Inventors: Tahua Yang, Woodridge; Sherwin Shang, Vernon Hills; Joel Warren, Palatine; Samuel Ding, Libertyville; Michael T. K. Ling, Vernon Hills; Lecon Woo, Libertyville, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/685,651

(22) Filed: Oct. 10, 2000

(51) Int. Cl.⁷ .......................... C08L 23/00; C08L 23/04
(52) U.S. Cl. ........................ 525/191; 525/240; 523/113; 602/41; 602/42; 602/48; 602/52; 604/6.16; 604/8; 604/19
(58) Field of Search ................................ 525/191, 240; 523/113; 602/41, 42, 48, 52; 604/6.16, 8, 19

(56) References Cited

U.S. PATENT DOCUMENTS

| | | |
|---|---|---|
| 2,705,223 A | 3/1955 | Renfrew et al. |
| 2,971,876 A | 2/1961 | Phair |
| 3,255,923 A | 6/1966 | Soto |
| 3,375,300 A | 3/1968 | Ropp |
| 3,494,897 A | 2/1970 | Reading et al. |
| 3,514,359 A | 5/1970 | Frese |
| 3,772,136 A | 11/1973 | Workman |
| 3,912,843 A | 10/1975 | Brazier |
| 3,937,758 A | 2/1976 | Castagna |
| 3,995,084 A | 11/1976 | Berger et al. |
| 4,041,103 A | 8/1977 | Davison et al. |
| 4,058,647 A | 11/1977 | Inoue et al. |
| 4,087,587 A | 5/1978 | Shida et al. |
| 4,087,588 A | 5/1978 | Shida et al. |
| 4,095,012 A | 6/1978 | Schirmer |
| 4,110,303 A | 8/1978 | Gergen et al. |
| 4,147,827 A | 4/1979 | Breidt, Jr. et al. |
| 4,233,367 A | 11/1980 | Ticknor et al. |
| 4,322,465 A | 3/1982 | Webster |
| 4,322,480 A | 3/1982 | Tuller et al. |
| 4,327,726 A | 5/1982 | Kwong |
| 4,332,655 A | 6/1982 | Berejka |
| 4,336,352 A | 6/1982 | Sakurai et al. |
| 4,387,184 A | 6/1983 | Coquard et al. |
| 4,405,667 A | 9/1983 | Christensen et al. |
| 4,407,877 A | 10/1983 | Rasmussen |
| 4,407,888 A | 10/1983 | Crofts |
| 4,417,753 A | 11/1983 | Bacebowski et al. |
| 4,429,076 A | 1/1984 | Saito et al. |
| 4,479,989 A | 10/1984 | Mahal |
| 4,521,437 A | 6/1985 | Storms |
| 4,548,348 A | 10/1985 | Clements |
| 4,562,118 A | 12/1985 | Maruhashi et al. |
| 4,568,723 A | 2/1986 | Lu |
| 4,573,994 A | 3/1986 | Fischell et al. |
| 4,588,648 A | 5/1986 | Krueger et al. |
| 4,599,276 A | 7/1986 | Martini |
| 4,627,844 A | 12/1986 | Schmitt |
| 4,628,969 A | 12/1986 | Jurgens, Jr. et al. |
| 4,636,412 A | 1/1987 | Field |

(List continued on next page.)

FOREIGN PATENT DOCUMENTS

| | | |
|---|---|---|
| DE | 251 904 A3 | 12/1987 |
| DE | 39 37 865 A1 | 6/1990 |
| DE | 41 42 271 A1 | 6/1993 |
| EP | 92897 | 2/1983 |
| EP | 0 156 464 A1 | 10/1985 |
| EP | 0 216 509 B1 | 8/1986 |
| EP | 0 283 164 | 3/1988 |
| EP | 0 291 208 | 4/1988 |
| EP | 0 291 208 A2 | 11/1988 |
| EP | 0 492 982 B1 | 12/1991 |
| EP | 0 497 567 A2 | 1/1992 |
| EP | 0 524 802 A1 | 1/1993 |
| EP | 446505 A1 | 6/1993 |
| EP | 0 582 355 B1 | 2/1994 |
| EP | 0 680 401 B1 | 11/1995 |
| EP | 0 430 585 B1 | 1/1996 |
| EP | 0 156 464 B1 | 5/1996 |
| EP | 0 709 105 A1 | 5/1996 |
| EP | 0 203 799 B1 | 8/1996 |
| EP | 0 384 694 B1 | 9/1996 |
| EP | 0 497 567 B1 | 9/1996 |
| EP | 0 790 063 A1 | 8/1997 |
| FR | 2688511 | 9/1993 |
| GB | 2 177 974 A | 2/1987 |
| JP | 03095286 | 4/1991 |
| JP | 05277154 | 10/1993 |
| JP | 11071554 | 3/1999 |
| WO | WO83/00158 | 1/1983 |
| WO | WO 86/07010 | 12/1986 |
| WO | WO 93 23 093 | 11/1993 |
| WO | WO 97/08054 | 6/1997 |
| WO | WO 98/27926 | 2/1998 |
| WO | 98/44043 | 10/1998 |
| WO | 98/48990 | 9/1999 |

*Primary Examiner*—Nathan M. Nutter
(74) *Attorney, Agent, or Firm*—Paula J. F. Kelly; Joseph P. Reagen; Wallenstein & Wagner (57) ABSTRACT

The present invention provides a polymer blend for fabricating medical products. The blend has a first ethylene and α-olefin copolymer obtained using a single-site catalyst present in an amount by weight of from about 0% to about 99% by weight of the blend and having a melt flow index from about 0.1 g/10 min to about 5 g/10 min, a second ethylene and α-olefin copolymer obtained using a single-site catalyst and being present in an amount by weight of the blend from about 0% to about 99% and having a melt flow index from higher than about 5 g/10 min to about 20 g/10 min; and a third ethylene and α-olefin copolymer obtained using a single-site catalyst and being present in an amount by weight of the blend from about 0% to about 99% and having a melt flow index greater than about 20 g/10 min.

107 Claims, 3 Drawing Sheets

U.S. PATENT DOCUMENTS

| | | | |
|---|---|---|---|
| 4,640,870 | A | 2/1987 | Akazawa et al. |
| 4,643,926 | A | 2/1987 | Mueller |
| 4,686,125 | A | 8/1987 | Johnston et al. |
| 4,692,361 | A | 9/1987 | Johnson et al. |
| 4,707,389 | A | 11/1987 | Ward |
| 4,724,028 | A | 2/1988 | Zabielski et al. |
| 4,726,997 | A | 2/1988 | Mueller et al. |
| 4,732,795 | A | 3/1988 | Ohya et al. |
| 4,734,327 | A | 3/1988 | Vicik |
| 4,735,855 | A | 4/1988 | Wofford et al. |
| 4,740,582 | A | 4/1988 | Coquard et al. |
| 4,753,222 | A | 6/1988 | Morishita |
| 4,760,114 | A | 7/1988 | Haaf et al. |
| 4,764,404 | A | 8/1988 | Genske et al. |
| 4,767,651 | A | 8/1988 | Starczewski et al. |
| 4,772,497 | A | 9/1988 | Maasola |
| 4,778,697 | A | 10/1988 | Genske et al. |
| 4,792,488 | A | 12/1988 | Schirmer |
| 4,795,782 | A | 1/1989 | Lutz et al. |
| 4,800,129 | A | 1/1989 | Deak |
| 4,803,102 | A | 2/1989 | Raniere et al. |
| 4,834,755 | A | 5/1989 | Silvestrini et al. |
| 4,855,356 | A | 8/1989 | Holub et al. |
| 4,856,259 | A | 8/1989 | Woo et al. |
| 4,856,260 | A | 8/1989 | Woo et al. |
| 4,863,996 | A | 9/1989 | Nakazima et al. |
| 4,871,799 | A | 10/1989 | Kobayashi et al. |
| 4,873,287 | A | 10/1989 | Sauers et al. |
| 4,877,682 | A | 10/1989 | Raniere et al. |
| 4,885,119 | A | 12/1989 | Mueller et al. |
| 4,910,085 | A | 3/1990 | Gogolewski et al. |
| 4,923,470 | A | 5/1990 | Dumican |
| 4,929,479 | A | 5/1990 | Shishido et al. |
| 4,931,520 | A | 6/1990 | Yamanashi et al. |
| 4,957,966 | A | 9/1990 | Nishio et al. |
| 4,957,967 | A | 9/1990 | Mizuno et al. |
| 4,966,795 | A | 10/1990 | Genske et al. |
| 4,977,213 | A | 12/1990 | Giroud-Abel et al. |
| 4,992,511 | A | 2/1991 | Yamamoto et al. |
| 4,996,054 | A | 2/1991 | Pietsch et al. |
| 4,999,254 | A | 3/1991 | Ofstein |
| 5,003,019 | A | 3/1991 | Ishimaru et al. |
| 5,006,601 | A | 4/1991 | Lutz et al. |
| 5,008,356 | A | 4/1991 | Ishimaru et al. |
| 5,017,652 | A | 5/1991 | Abe et al. |
| 5,034,457 | A | 7/1991 | Serini et al. |
| 5,034,458 | A | 7/1991 | Serini et al. |
| 5,053,457 | A | 10/1991 | Lee |
| 5,071,686 | A | 12/1991 | Genske et al. |
| 5,071,911 | A | 12/1991 | Furuta et al. |
| 5,071,912 | A | 12/1991 | Furuta et al. |
| 5,075,376 | A | 12/1991 | Furuta et al. |
| 5,079,295 | A | 1/1992 | Furuta et al. |
| 5,085,649 | A | 2/1992 | Flynn |
| 5,087,677 | A | 2/1992 | Brekner et al. |
| 5,093,164 | A | 3/1992 | Bauer et al. |
| 5,093,194 | A | 3/1992 | Touhsaent et al. |
| 5,094,921 | A | 3/1992 | Itamura et al. |
| 5,108,844 | A | 4/1992 | Blemberg et al. |
| 5,110,642 | A | 5/1992 | Genske |
| 5,116,906 | A | 5/1992 | Mizuno et al. |
| 5,129,894 | A | 7/1992 | Sommermeyer et al. |
| 5,132,363 | A | 7/1992 | Furuta et al. |
| 5,135,785 | A | 8/1992 | Millon |
| 5,145,731 | A | 9/1992 | Lund et al. |
| 5,154,979 | A | 10/1992 | Kerschbaumer et al. |
| 5,159,004 | A | 10/1992 | Furuta et al. |
| 5,164,267 | A | 11/1992 | D'Heur et al. |
| 5,176,634 | A | 1/1993 | Smith et al. |
| 5,176,956 | A | 1/1993 | Jevne et al. |
| 5,183,706 | A | 2/1993 | Bekele |
| 5,185,189 | A | 2/1993 | Stenger et al. |
| 5,189,091 | A | 2/1993 | Laughner |
| 5,194,316 | A | 3/1993 | Horner et al. |
| 5,196,254 | A | 3/1993 | Akiyama |
| 5,206,290 | A | 4/1993 | Mizuno et al. |
| 5,207,983 | A | 5/1993 | Liebert et al. |
| 5,212,238 | A | 5/1993 | Schelbelhoffer et al. |
| 5,218,048 | A | 6/1993 | Abe et al. |
| 5,218,049 | A | 6/1993 | Yamamoto et al. |
| 5,230,934 | A | 7/1993 | Sakano et al. |
| 5,230,935 | A | 7/1993 | Delimoy et al. |
| 5,238,997 | A | 8/1993 | Bauer et al. |
| 5,244,971 | A | 9/1993 | Dekoninck |
| 5,258,230 | A | 11/1993 | LaFleur et al. |
| 5,272,235 | A | 12/1993 | Wakatsuru et al. |
| 5,278,231 | A | 1/1994 | Chundury |
| 5,288,560 | A | 2/1994 | Sudo et al. |
| 5,288,799 | A | 2/1994 | Schmid et al. |
| 5,290,856 | A | 3/1994 | Okamoto et al. |
| 5,306,542 | A | 4/1994 | Bayer |
| 5,312,867 | A | 5/1994 | Mitsuno et al. |
| 5,317,059 | A | 5/1994 | Chundury et al. |
| 5,331,057 | A | 7/1994 | Brekner et al. |
| 5,342,886 | A | 8/1994 | Glotin et al. |
| 5,348,794 | A | 9/1994 | Takahashi et al. |
| 5,356,676 | A | 10/1994 | von Widdern et al. |
| 5,359,001 | A | 10/1994 | Epple et al. |
| 5,371,151 | A | 12/1994 | Gelles et al. |
| 5,378,543 | A | 1/1995 | Murata et al. |
| 5,378,800 | A | 1/1995 | Mok et al. |
| 5,382,631 | A | 1/1995 | Stehling et al. |
| 5,387,645 | A | 2/1995 | Montag et al. |
| 5,422,409 | A | 6/1995 | Brekner et al. |
| 5,457,249 | A | 10/1995 | Toshihiro et al. |
| 5,475,060 | A | 12/1995 | Brekner et al. |
| 5,498,677 | A | 3/1996 | Wellner et al. |
| 5,534,606 | A | 7/1996 | Bennett et al. |
| 5,552,504 | A | 9/1996 | Bennett et al. |
| 5,583,192 | A | 12/1996 | Bennett et al. |
| 5,610,253 | A | 3/1997 | Hatke et al. |
| 5,620,425 | A | 4/1997 | Heffernan et al. |
| 5,629,398 | A | 5/1997 | Okamoto et al. |
| 5,637,100 | A | 6/1997 | Sudo |
| 5,637,400 | A | 6/1997 | Brekner et al. |
| 5,650,471 | A | 7/1997 | Abe et al. |
| 5,686,527 | A | 11/1997 | Laurin et al. |
| 5,693,728 | A | 12/1997 | Okamoto et al. |
| 5,698,645 | A | 12/1997 | Weller et al. |
| 5,707,751 | A * | 1/1998 | Garza et al. ................ 428/515 |
| 5,723,189 | A | 3/1998 | Sudo |
| 5,733,991 | A | 3/1998 | Rohrmann et al. |
| 5,744,664 | A | 4/1998 | Brekner et al. |
| 5,756,623 | A | 5/1998 | Krueder et al. |
| 5,788,670 | A | 8/1998 | Reinhard et al. |
| 5,792,824 | A | 8/1998 | Natori |
| 5,795,945 | A | 8/1998 | Natori |
| 5,849,843 | A | 12/1998 | Laurin et al. |
| 5,854,347 | A | 12/1998 | Laurin et al. |
| 5,854,349 | A | 12/1998 | Abe et al. |
| 5,863,986 | A | 1/1999 | Herrmann-Schönherr et al. |
| 5,872,201 | A | 2/1999 | Cheung et al. |
| 5,980,495 | A | 11/1999 | Heinz et al. |
| 5,990,254 | A | 11/1999 | Weller et al. |
| 5,993,949 | A | 11/1999 | Rosenbaum et al. |
| 5,998,019 | A | 12/1999 | Rosenbaum et al. |
| 6,007,520 | A | 12/1999 | Sudo |
| 6,020,444 | A | 2/2000 | Riedel et al. |
| 6,060,572 | A | 5/2000 | Gillis et al. |
| 6,065,270 | A | 5/2000 | Reinhard et al. |

| | | | | | | |
|---|---|---|---|---|---|---|
| 6,068,936 A | | 5/2000 | Peiffer et al. | 6,261,655 B1 | 1/2001 | Rosenbaum et al. |
| 6,110,549 A | * | 8/2000 | Hamada et al. ............ 428/35.2 | 6,225,426 B1 | 5/2001 | Gillis et al. |
| 6,121,394 A | | 9/2000 | Sugimoto et al. | 6,225,427 B1 | 5/2001 | Burton et al. |
| 6,136,744 A | | 10/2000 | Gillis et al. | RE37,208 E | 6/2001 | Winter et al. |
| 6,147,025 A | | 11/2000 | Gillis et al. | 6,255,396 B1 | 7/2001 | Ding et al. |
| 6,168,862 B1 | | 1/2001 | Rosenbaum et al. | | | |
| 6,169,052 B1 | | 1/2001 | Brekner | | | |

* cited by examiner

BLUE OUTLET PORT CLAMPS

BLEND OF ETHYLENE AND α-OLEFIN COPOLYMERS OBTAINED USING A METALLOCENE CATALYST FOR FABRICATING MEDICAL FILMS AND TUBINGS

TECHNICAL FIELD

This invention relates to a polymer blend for fabricating medical materials and more particularly, to a blend of ethylene and α-olefin copolymers each having a narrow molecular weight distribution for fabricating medical films and tubings.

BACKGROUND ART

In the medical field, where beneficial agents are collected, processed and stored in containers, transported and ultimately delivered through tubes by infusion to patients, there has been a recent trend toward developing materials useful for fabricating such containers and tubing without the disadvantages of currently used materials such as polyvinyl chloride. These new materials for tubings must have a unique combination of properties, so that the tubing may be used in peritoneal dialysis and I.V. administration sets. Among these are the materials must be optically clear, environmentally compatible, have sufficient yield strength and flexibility, have a low quantity of low molecular weight additives, have good dimensional stability and be compatible with medical solutions.

It is desirable for medical tubing to be optically transparent to allow for visual inspection of fluids in the tubing.

It is also a requirement that the tubing materials be environmentally compatible as a significant quantity of medical tubing is disposed of in landfills and through incineration. Further benefits are realized by using a material that is thermoplastically recyclable so that scrap generated during manufacturing may be incorporated into virgin material and refabricated into other useful articles.

For tubing that is disposed of by incineration, it is necessary to use a material that does not generate or minimizes the formation of by-products such as inorganic acids which may be environmentally harmful, irritating, and corrosive. For example, PVC may generate objectionable amounts of hydrogen chloride (or hydrochloric acid when contacted with water) upon incineration.

To be compatible with medical or dialysis solutions, it is desirable that the tubing material be free from or have a minimal content of low molecular weight additives such as plasticizers, stabilizers and the like. These components could be extracted into the dialysis or therapeutic solutions that come into contact with the material. The additives may react with the solutions or otherwise render the solutions ineffective.

Polyvinyl chloride ("PVC") has been widely used to fabricate medical tubings as it meets most of these requirements. However, because PVC by itself is a rigid polymer, low molecular weight components known as plasticizers must be added to render PVC flexible. As set forth above, these plasticizers may leach out of the tubing and into the fluid passing through the tubing to contaminate the fluid. For this reason, and because of the difficulties encountered in incinerating PVC, there is a need to replace PVC medical tubing.

Polyolefins have been developed which meet many of the requirements of medical containers and tubing, without the disadvantages associated with PVC. Polyolefins typically are compatible with medical applications because they have minimal extractability to the fluids and contents which they contact. Most polyolefins are environmentally sound as they do not generate harmful degradants upon incineration, and in most cases are capable of being thermoplastically recycled. Many polyolefins are cost effective materials that may provide an economic alternative to PVC. However, there are many hurdles to overcome to replace all the favorable attributes of PVC with a polyolefin.

One particular polyolefin of interest is an ethylene and α-olefin copolymer obtained using a single-site catalyst such as a metallocene catalyst, a vanadium catalyst or the like. Of this group of copolymers those having a density of less than about 0.915 g/cc are most desirable due to their favorable modulus of elasticity and other physical characteristics. These copolymers obtained using a single site catalyst shall be referred to as ultra-low density polyethylene (m-ULDPE). The m-ULDPE copolymers have better clarity and softness, a low level of extractables and also have fewer additives than traditional polyolefins. This is largely due to m-ULDPE having a narrow molecular weight distribution and a narrow composition distribution. The m-ULDPE is a newly commercialized resin that recently has been used in food and some medical applications.

The major technical challenges of using m-ULDPE to fabricate medical tubing or films is to overcome a melt fracture phenomenon that readily occurs in these type of polymers during processing. Melt fracture is typically and easily generated in this family of resins because they display significantly less rheological shear thinning during extrusion when compared to other ULDPE resins obtained using traditional Ziegler-Natta type catalysts. Melt fracture occurs when the surface of the extrudate reaches an unstable flow pattern when the extrusion speed exceeds certain levels. The unstable flow pattern leads to a structural and cosmetic defect in the surface of the finished product which is sometimes referred to as "shark skin" due to its textured finish. The melt fracture phenomenon significantly limits the range of output rates in which these resins can be processed without experiencing melt fracture and in most cases the rate falls outside the desired output rate of commercial extrusion processes. The resin industry has attempted to overcome this challenge by introducing fluoro-polymer based processing aids. The use of such processing aids is undesirable in the medical industry as such additives may leach into the solutions or generate inorganic acids upon incineration.

Currently, there are efforts in dealing with melt fracture without introducing foreign additives into the material formulations. One is to raise the melt temperature, but has a potential drawback of widening the dimensional tolerance due to longer cooling period of the extrudate which in turn can lead to dimensional tolerance problems and slow the extrusion rate. Another is to apply surface coat of fluoropolymer on the die surface to reduce extrusion friction resistance. Both have been proved not effective for fabricating medical products but may be effective in manufacturing other products. Another effort is to blend a variety of polymers. Blending different polymers to achieve desired product performance is commonly used in the plastics industry. However, the impacts of the miscibility of the resins on the mechanical properties are always one of the major criteria in selecting individual polymers before blending. Products with high haze values are usually generated with mismatched resin densities or refractive indicies.

SUMMARY OF THE INVENTION

The present invention provides a blend of m-ULDPE resins or similar resins with a narrow molecular weight distribution for high speed production of medical products such as tubings or films with no melt fracture, good dimensional control, and high production throughput rate.

The present invention provides a polymer blend for fabricating medical products. The blend has a first ethylene and α-olefin copolymer obtained using a single site catalyst present in an amount by weight of from about 0% to about 99% by weight of the blend and having a melt flow index from fractional, such as about 0.1 g/10 min, to about 5 g/10 min, a second ethylene and α-olefin copolymer obtained using a single site catalyst and being present in an amount by weight of the blend from about 0% to about 99% and having a melt flow index from higher than about 5 g/10 min to about 20 g/10 min; and a third ethylene and α-olefin copolymer obtained using a single-site catalyst and being present in an amount by weight of the blend from about 0% to about 99% and having a melt flow index greater than about 20 g/10 min.

The present invention further provides a polymer blend for fabricating medical products. The blend has a first ethylene and α-olefin copolymer having a molecular weight distribution of less than about 3 and being present in an amount by weight of from about 0% to about 99% by weight of the blend and having a melt flow index from about 0.1 g/10 min to about 5 g/10 min, a second ethylene and α-olefin copolymer having a molecular weight distribution of less than about 3 and being present in an amount by weight of the blend of from about 0% to about 99% and having a melt flow index from higher than about 5 g/10 min to about 20 g/10 min, and a third ethylene and α-olefin copolymer having a molecular weight distribution of less than about 3 and being present in an amount by weight of the blend from about 0% to about 99% and having a melt flow index greater than about 20 g/10 min.

The present invention further provides a medical tubing having a sidewall of a polymer blend. The blend has a first ethylene and α-olefin copolymer having a molecular weight distribution of less than about 3 and being present in an amount by weight of from about 0% to about 99% by weight of the blend and having a melt flow index from about 0.1 g/10 min to about 5 g/10 min, a second ethylene and α-olefin copolymer having a molecular weight distribution of less than about 3 and being present in an amount by weight of the blend of from about 0% to about 99% and having a melt flow index from higher than about 5 g/10 min to about 20 g/10 min, and a third ethylene and α-olefin copolymer having a molecular weight distribution of less than about 3 and being present in an amount by weight of the blend from about 0% to about 99% and having a melt flow index greater than about 20 g/10 min.

The present invention further provides a medical film of a polymer blend. The polymer blend having a first ethylene and α-olefin copolymer having a molecular weight distribution of less than about 3 and being present in an amount by weight of from about 0% to about 99% by weight of the blend and having a melt flow index from about 0.1 g/10 min to about 5 g/10 min, a second ethylene and α-olefin copolymer having a molecular weight distribution of less than about 3 and being present in an amount by weight of the blend of from about 0% to about 99% and having a melt flow index from higher than about 5 g/10 min to about 20 g/10 min, and a third ethylene and α-olefin copolymer having a molecular weight distribution of less than about 3 and being present in an amount by weight of the blend from about 0% to about 99% and having a melt flow index greater than about 20 g/10 min.

DETAILED DESCRIPTION OF THE DRAWINGS

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention provides non-PVC containing polymer blends for fabricating medical and food product such as tubings, films and containers and the like fabricated therefrom. The blends of the present invention are of olefin containing polymers having a narrow molecular weight distribution. The blends are capable of being processed at the rates required by commercial processing equipment and provide tubings and films having favorable surface characteristics, dimensional stability, modulus of elasticity, softness, optical clarity and yield strength.

The blends of the present invention have at least two polymeric components. In a preferred form of the invention the blends have three or more components.

Suitable polymers of the present invention are selected from ethylene and α-olefin copolymers preferably having a density, as measured by ASTM D-792 of less than about 0.915 g/cc and are commonly referred to as very low density polyethylene (VLDPE), ultra low density ethylene (ULDPE) and the like. The α-olefin should have from 3–17 carbons, more preferably from 4–12 and most preferably 4–8 carbons. In a preferred form of the invention, the ethylene and α-olefin copolymers are obtained using a single-site catalysts. Suitable single-site catalyst systems, among others, are those disclosed in U.S. Pat. Nos. 5,783,638 and 5,272,236. Suitable ethylene and α-olefin copolymers include those sold by Dow Chemical Company under the AFFINITY tradename, Dupont-Dow under the ENGAGE tradename and Exxon under the EXACT tradename.

In preferred form of the invention the components of the blend with have refractive indicies that differ by equal to or less than 0.08, more preferably equal to or less than 0.04 and most preferably equal to or less than 0.01. Also, in a preferred form of the invention, the components of the blend will have a difference in their densities of equal to or less than 0.008 g/cc, more preferably equal to or less than 0.004 g/cc and most preferably equal to or less than 0.002 g/cc.

These m-ULDPE resins have narrow molecular weight distributions. What is meant by molecular weight distribution is $M_w/M_n$ where $M_w$ is the weight average molecular weight and $M_n$ is the number average molecular weight. What is meant by the term narrow molecular weight distribution is that $M_w/M_n$ is less than about 3, more preferably less than about 2.8 and most preferably less than about 2.5

To overcome the difficulty in processing these resins at high speed throughputs the present invention provides blending ULDPE resins having varying melt indicies. The term "melt flow" and "melt flow index" is used herein as the amount, in grams, of a thermoplastic resin which can be forced through a given orifice under a specified pressure and temperature within 10 minutes. The value should be determined in accordance with ASTM D 1238. For two component blends having a first and a second ULDPE the first ULDPE will have a melt index of from 0.1 g/10 min to about 5 g/10 min and the second ULDPE will have a melt flow index of greater than or equal to about 5 g/10 min.

In a preferred form of the invention the blend has a first, second and third ULDPE resin. The first ULDPE resin will have a melt index from about 0.1 g/10 min to about 5 g/10 min, the second ULDPE resin will have a melt index of from higher than about 5 g/10 min to about 20 g/10 min and the third ULDPE resin will have a melt flow index of greater than about 20 g/10 min. The first, second and third ULDPE resins can be present in an amount from about 0% to about 99% by weight of the blend, more preferably from about 5% to about 70% and most preferably in substantially equal amounts by weight.

Figure 4:
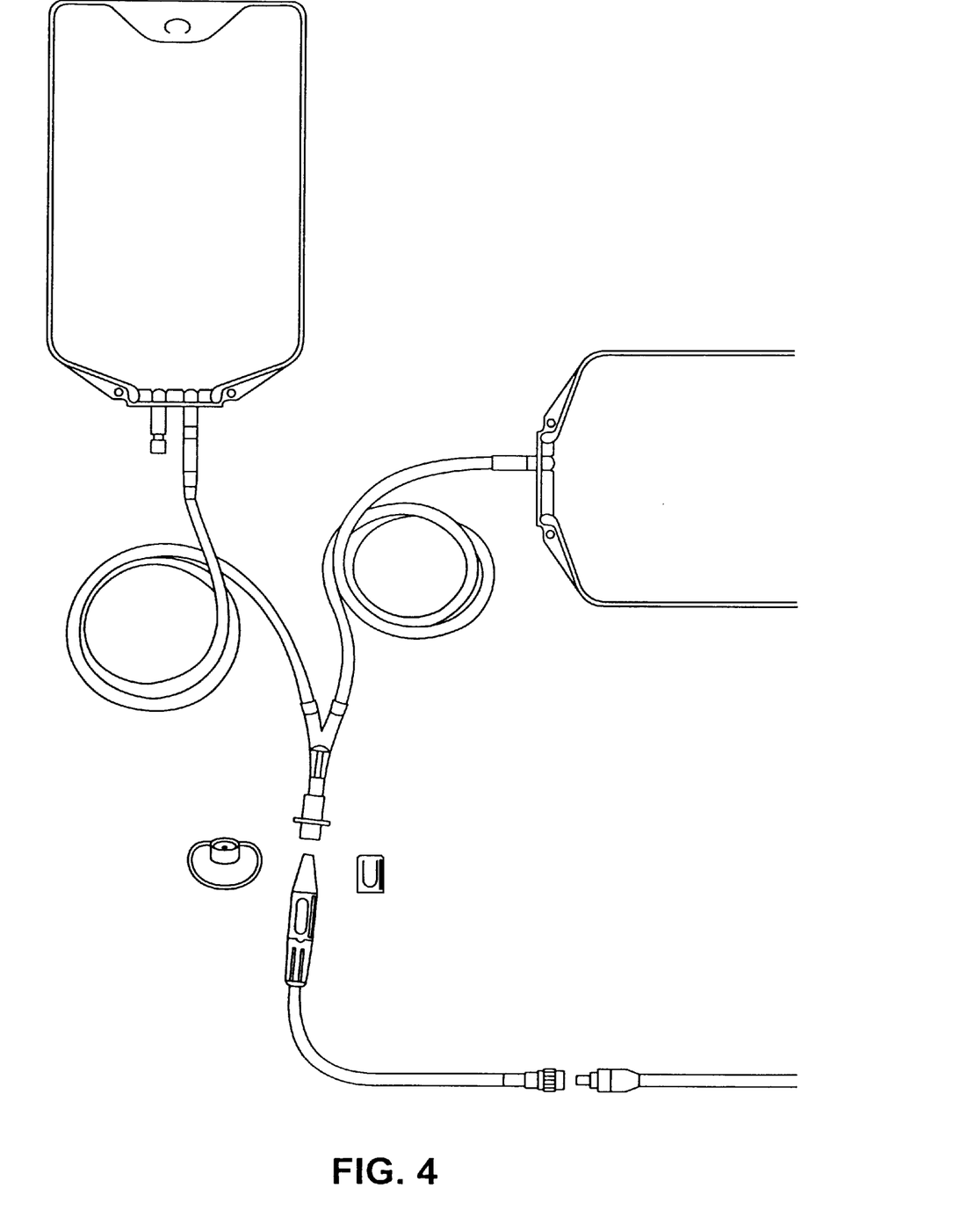
FIG. 4 is a plan view of a peritoneal dialysis administration set.
Figure 5:
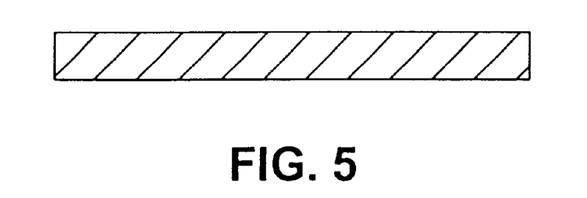
FIG. 5 is a cross-sectional view of a monolayer film.
Figure 6:
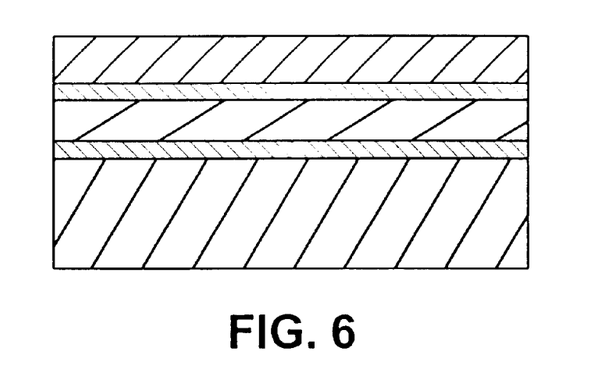
FIG. 6 is cross-sectional view of a multiple layered film.

The blends of the present invention are capable of being fabricated into monolayer tubings (FIG. 1), multiple layered tubings (FIG. 2), a multiple lumen tubing (FIG. 3), monolayer films (FIG. 5) and multiple layered films (FIG. 6). FIG. 4 shows a peritoneal dialysis administration set 20 having tubing 22 and a container 24 fabricated from the tubing and films of the present invention. The blends can be fabricated at commercial processing rates and provide dimensionally stable products without experiencing the shark skin appearance in the finished product which is indicative of melt fracture.

Figures 1, 2, 3:
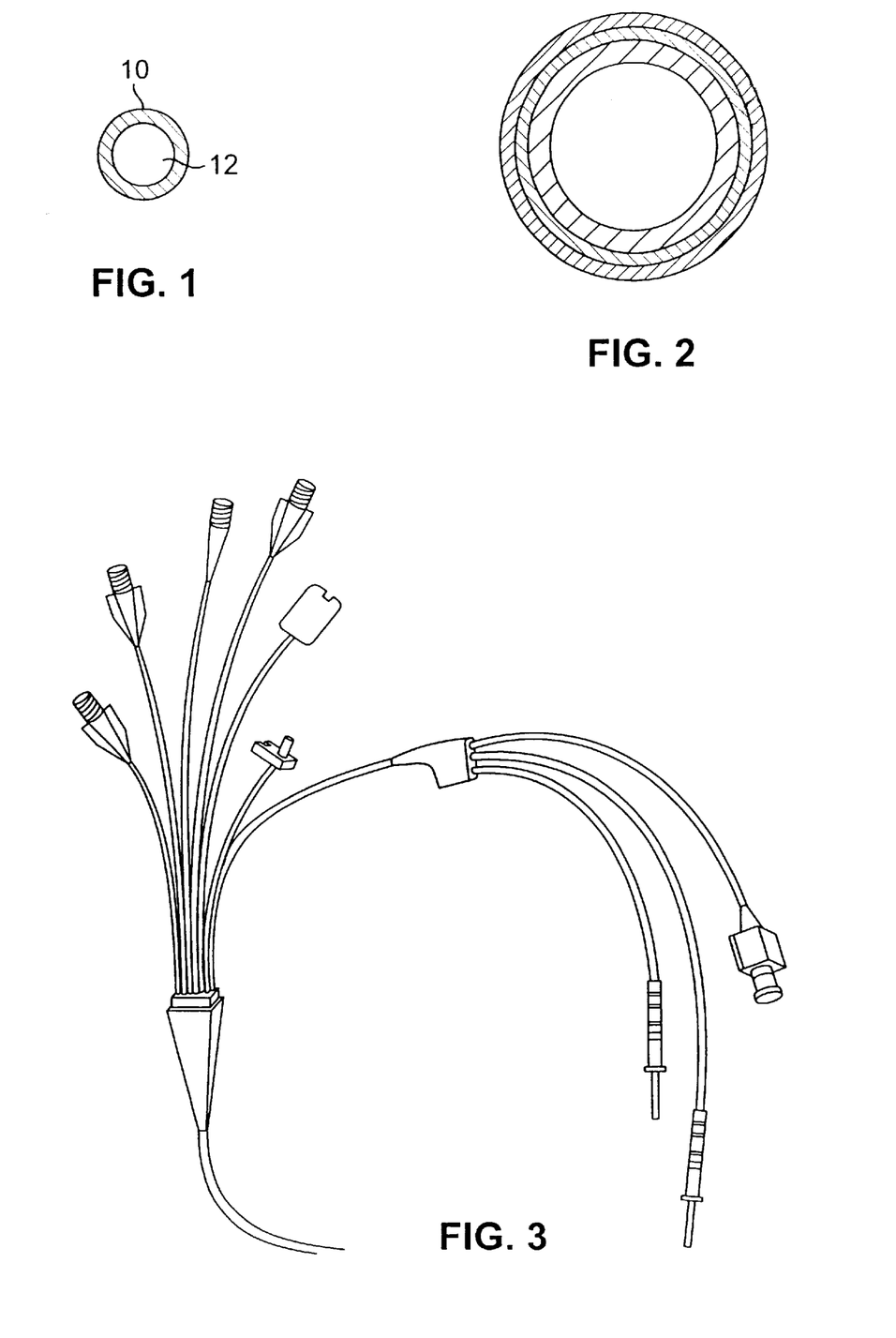
FIG. 1 is a cross-sectional view of a monolayer tubing.
FIG. 2 is a cross-sectional view of a multiple layered tubing.
FIG. 3 is a plan view of a multiple lumen tubing.

The tubings shown in FIGS. 1, 2 and 3 shall have the following physical properties: a modulus of elasticity of less than about 30,000 psi, more preferably less than about 20,000 and most preferably less than about 10,000 psi, an internal haze of less than about 25% when measured in accordance with ASTM D1003, is capable of being fabricated at a throughput rate of greater than about 100 ft/min, more preferably greater than about 200 ft/min, even more preferably greater than about 300 ft/min and most preferably equal to or greater than about 350 ft/min; has a substantially smooth surface absent a shark skin appearance which is indicative of melt fracture, has less than about 10 mg of low molecular weight extractible components, good dimensional stability, a yield strength of from about 500 psi to about 1000 psi and more preferably from about 600 psi to about 800 psi, is capable of being repeatedly used with a medical tubing clamp with an occlusion force typically of about 5 lbs without significantly damaging the tubing and is capable of solvent bonding to a rigid component.

What is meant by "smooth surface" is that the surface of the tubing or film does not have a substantial of significant quantity of imperfections known in the field as "shark skin." The tubing or film is smooth to the touch and smooth in appearance to the naked eye. This can be quantified by a melt fracture number as follows: 1 tubing turns opaque and displays severe shark skin pattern, 2 tubing is translucent and shark skin appearance is obvious, 3 tubing is clear with light shark skin appearance, and 4 tubing is clear with no shark skin appearance.

What is meant by "low molecular weight extractible component" is the amount of material extracted from a 635 cm² piece of test material extracted at 70° C. for 24 hours in 106 ml of USP purified water.

What is meant by the term "yield strength" is the quantity resulting from dividing the load point by the original cross-sectional thickness area of the specimen and measured according to ASTM D-882.

What is meant by the term "good dimensional stability" is that the process capability $C_P$ of the inner diameter of the tubing (I.D.), the outer diameter (O.D.) and the tubing wall thickness shall be greater than about 1.33 for a dimensional tolerance of +/−1.7% of O.D., 2.5% of I.D., and 10% of wall thickness. $C_P$ is the specification width (or the range between upper and lower specification limits) divided by the process width (or 6 times the standard deviation). The $C_P$ is measured on-line by a BETA LAZERMIKE Model 163-100-05.

Figure 7:
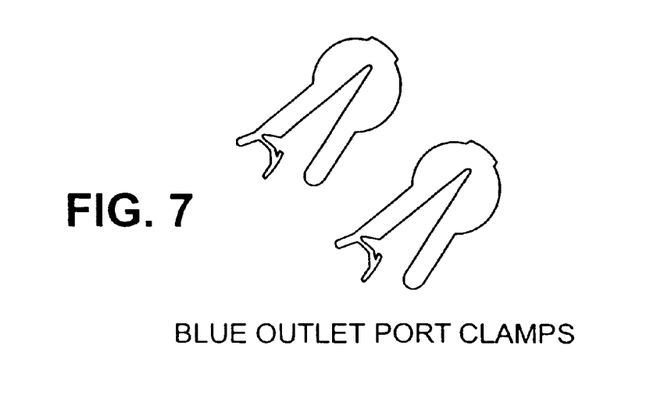
FIG. 7 is a perspective view of typical medical tubing clamp for use in I.V. administration sets and peritoneal dialysis administration sets.

The tubing of the present invention can be used with a medical tubing clamp such as the ones shown in FIG. 7. A medical tubing clamp 50 is used to control the flow rate of fluid passing through the medical tubing. The medical tubing clamp 52 has a slot 54 through which the tubing is placed. The slot 54 narrows from a diameter greater than the O.D. of the tubing to a point smaller than the O.D. of the tubing. By moving the tubing in the slot the tubing sidewalls can occlude the flow of fluid through the tubing. The tubing must have sufficient lubricity for the clamp to be used without severing the tubing or without permanently occluding the tubing under a typical occluding force applied by the claim of about 5 lbs.

What is meant by the term solvent bonding is that the tubing can be exposed to a solvent to melt, dissolve or swell the tubing and then be attached to another polymeric component to form a permanent bond. Suitable solvents typically include those having a solubility parameter of less than about 20 $(MPa)^{1/2}$, more preferably less than about 19 $(MPa)^{1/2}$ and most preferably less than about 18 $(MPa)^{1/2}$ and include, but are not limited to, aliphatic hydrocarbons, aromatic hydrocarbons, mixtures of aliphatic hydrocarbons, mixtures of aromatic hydrocarbons and mixtures of aromatic and aliphatic hydrocarbons. Suitable aliphatic hydrocarbons include substituted and unsubstituted hexane, heptane, cyclohexane, cycloheptane, decalin, and the like. Suitable aromatic hydrocarbons include substituted and unsubstituted aromatic hydrocarbon solvents such as xylene, tetralin, toluene, and cumene. Suitable hydrocarbon substituents include aliphatic substituents having from 1–12 carbons and include propyl, ethyl, butyl, hexyl, tertiary butyl, isobutyl and combinations of the same. What is meant by the terms "aliphatic hydrocarbon" and "aromatic hydrocarbon" is a compound containing only carbon and hydrogen atoms. Suitable solvents will also have a molecular weight less than about 200 g/mole, more preferably less than about 180 g/mole and most preferably less than about 140 g/mole.

What is meant by a "rigid component" is a connector or other device commonly used in peritoneal dialysis or I.V. administration sets and typically having a modulus of elasticity of greater than about 30,000 psi. Suitable polymers for fabricating a rigid component includes homopolymers and copolymers of polypropylenes, polyesters, polyamdies, polycarbonates, cylic olefin containing polymers and bridged polycyclic olefin containing polymers. Suitable cyclic olefin containing polymers and bridged polycylic olefin containing polymers are disclosed in U.S. patent application Nos. 09/393,912, 09/393,052, 09/393,051 which are incorporated herein by reference and made a part hereof.

The film shown in FIGS. 5 and 6 shall have the following physical characteristics measured in accordance with the details provided above: a modulus of elasticity of less than about 30,000 psi, an internal haze of less than about 25%, capable of being fabricated at a throughput rate of greater than about 300 ft/min, more preferably greater than about 400 ft/min and most preferably greater than about 500 ft/min; has a substantially smooth surface absent of a shark skin appearance, good dimensional stability, has less than about 10 mg of low molecular weight extractible components, and a yield strength of from about 500 psi to about 1000 psi and more preferably from about 600 psi to about 800 psi.

The blends of the present invention can be provided individually and blended by tumble blending or using standard Banburry type mixers, or twin screw type mixers. It is also contemplated that the desired components can be blended, extruded and pellitized. It is also contemplated to prepare the desired blend of resins using series of reactors connected in sequence.

In a preferred form of the invention for the latter described process, there is a reactor provided for each of the polymers in the blend. Monomers and catalyst are added into the first reactor. The reaction conditions, particularly pressure, temperature, and residence time, are controlled so that the amount of product produced in each reactor is within certain limits and the product has certain properties. The catalyst used in each reactor is a metallocene catalyst or a blend with other metallocene catalyst or a blend with other catalyst. In the first reaction step, ethylene monomer, α-olefin comonomer, and catalyst are introduced into the first reactor.

In the first reactor, a ULDPE is produced with a melt flow index of from about 0.1 g/10 min to about 5 g/10 min. The ULDPE product and the unreacted monomers are transported to the second reactor. In the second reactor, additional ULDPE resin is produced with a melt flow index of greater than about 5 g/10 min to about 20 g/10 min. The two types of ULDPE polymers and the unreacted monomers are transported to the third reactor. In the final reactor, additional resin is produced with a melt flow index of greater than about 20 g/10 min. Each of the three reactor products will be present in the final product in an amount from about 0% to about 99% by weight of the blend, more preferably from about 5% to about 90%, and most preferably in substantially equal portions. Of course it is possible to produce the polymers in any sequence so that the higher melt flow index polymer is produced in the first, second or third reactor. The same is true for the other components. It is also possible to produce two components with two reactors or to produce more than 3 components as desired.

The use of multistage processes for polymerization to produce blends of resins of different molecular weights is well known. For example, U.S. Pat. No. 4,336,352 concerned polyethylene compositions consisting of three different polyethylenes. One alternative presented contains a three stage process. In the first stage polyethylene having a density between 0.94–0.98 g/cc is polymerized and the proportion of this fraction to the end product is 1–10%. In the next polymerization stage polyethylene having a density between 0.94–0.98 is produced. In the third polymerization step polyethylene having a density of 0.90–0.97 is produced. The final product has a melt index of 0.001–1 and a density of 0.935–0.976.

The blends can be fabricated into tubing using standard polymer processing techniques such as extrusion, coextrusion, blow extrusion, blow molding, injection molding and the like. Similarly the blends can be fabricated into films or sheetings using standard polymer processing techniques such as extrusion, coextrusion, blow extrusion, blow molding, compression molding injection molding, lamination, thermoforming, calendaring and the like.

The following are non-limiting examples of the present invention and should not be used to limit the scope of the claims set forth below.

EXAMPLES

The following m-ULDPE resins were used in fabricating two and three component blends.

| Materials | Refractive index | MWD | Density (g/cc) | MI (g/10 min) | Hardness Shore A | DSC Tm (° C.) | Ultimate Tensile strength (Mpa) | Ultimate Elongation (%) |
|---|---|---|---|---|---|---|---|---|
| Engage 8003 (A) | 1.501 | 2.39 | 0.885 | 1.0 | 86 | 76 | 30.3 | 700 |
| Engage 8411 (B) | 1.501 | 2.33 | 0.880 | 18 | 76 | 78 | 10.6 | 1000 |
| Engage 8401 (C) | 1.501 | 2.15 | 0.885 | 30 | 85 | 76 | 10.8 | >1000 |

The two and three component blends in the amounts specified in the table below were fabricated into medical tubings. The medical tubings had the noted physical characteristics.

| Resin Blend | MI (g/10 min) of the blend | Melt Temp (° F.) | Speed (FTPM) | Cp of I.D. | Cp of O.D. | Cp of wall thickness | Melt fracture |
|---|---|---|---|---|---|---|---|
| 75% A + 25% C | 1.56 | 348 | 200 | 0.74 | 0.74 | 2.22 | 1 |
| 50% A + 50% C | 5 | 347 | 200 | 1.10 | 1.10 | 4.43 | 2 |
| 45% A+ 45% B+ 10% C | 3 | 346 | 200 | 1.33 | 1.33 | 4.43 | 2 |
| 45% A + 45% B + 10% C | 3 | 346 | 250 | 0.70 | 0.84 | 2.95 | 2 |
| 33% A + 33% B + 33% C | 6.5 | 343 | 200 | 1.66 | 1.66 | 4.43 | 4 |
| 33% A + 33% B + +33% C | 6.5 | 333 | 350 | 1.66 | 1.90 | 4.43 | 4 |

While specific embodiments have been illustrated and described, numerous modifications are possible without departing from the spirit of the invention, and the scope of protection is only limited by the scope of the accompanying claims.

What is claimed is:

1. A polymer blend for fabricating medical products comprising:
   a first ethylene and α-olefin copolymer obtained using a single-site catalyst present in an amount by weight of from about 0% to about 99% by weight of the blend and having a melt flow index from about 0.1 g/10 min to about 5 g/10 min;
   a second ethylene and α-olefin copolymer obtained using a single-site catalyst and being present in an amount by weight of the blend from about 0% to about 99% and having a melt flow index from higher than about 5 g/10 min to about 20 g/10 min; and a third ethylene and α-olefin copolymer obtained using a single-site catalyst and being present in an amount by weight of the blend from about 0% to about 99% and having a melt flow index greater than about 20 g/10 min.

2. The blend of claim 1 wherein the first, second hand third ethylene and α-olefin copolymers are each present in an amount within the range of from about 5% to about 70% by weight of the blend.

3. The blend of claim 2 wherein the first, second and third ethylene and α-olefin copolymers are each present in substantially equal quantities by weight of the blend.

4. The blend of claim 1 when fabricated into a monolayer tubing has a modulus of elasticity of less than about 30,000 psi.

5. The blend of claim 1 when fabricated into a monolayer tubing has a modulus of elasticity of less than about 20,000 psi.

6. The blend of claim 1 when fabricated into a monolayer tubing has a modulus of elasticity of less than about 10,000 psi.

7. The blend of claim 4 when fabricated into a monolayer tubing has an internal haze less than about 25%.

8. The blend of 7 is capable of being fabricated into a monolayer tubing at a throughput rate of greater than about 100 ft/min.

9. The blend of 7 is capable of being fabricated into a monolayer tubing at a throughput rate of greater than about 200 fl/min.

10. The blend of 7 is capable of being fabricated into a monolayer tubing at a throughput rate of greater than about 300 ft/min.

11. The blend of 7 is capable of being fabricated into a monolayer tubing at a throughput rate of greater than about 350 ft/min.

12. The blend of claim 8 when fabricated into a monolayer tubing has a substantially smooth surface.

13. The blend of claim 1 wherein the first ethylene and α-olefin copolymer, the second ethylene and α-olefin copolymer and the third ethylene and α-olefin copolymer each have a refractive index with the refractive indicies differing by equal to or less than 0.08.

14. The blend of claim 1 wherein the first ethylene and α-olefin copolymer, the second ethylene and α-olefin copolymer and the third ethylene and α-olefin copolymer each have a refractive index with the refractive indicies differing by equal to or less than 0.04.

15. The blend of claim 1 wherein the first ethylene and α-olefin copolymer, the second ethylene and α-olefin copolymer and the third ethylene and α-olefin copolymer each have a refractive index with the refractive indicies differing by equal to or less than 0.01.

16. The blend of claim 1 when fabricated into a monolayer tubing has less than about 10 mg of low molecular weight extractible components.

17. The blend of claim 1 when fabricated into a monolayer tubing has a yield strength within the range of from about 500 psi to about 1000 psi.

18. The blend of claim 1 when fabricated into a monolayer tubing has a yield strength of from about 600 psi to about 1000 psi.

19. The blend of claim 1 when fabricated into a monolayer tubing is capable of being used with a medical tubing clamp without significantly damaging the tubing.

20. The blend of claim 1 when fabricated into a monolayer tubing is capable of solvent bonding to a rigid component.

21. The blend of claim 20 wherein the rigid component is fabricated from a cyclic olefin containing polymer or a bridged polycyclic hydrocarbon containing polymer.

22. The blend of claim 1 wherein the first ethylene and α-olefin copolymer, the second ethylene and α-olefin copolymer and the third ethylene and α-olefin copolymer each have a density differing by equal to or less than 0.008 g/cc.

23. The blend of claim 1 wherein the first ethylene and α-olefin copolymer, the second ethylene and α-olefin copolymer and the third ethylene and α-olefin copolymer each have a density differing by equal to or less than 0.004 g/cc.

24. The blend of claim 1 wherein the first ethylene and α-olefin copolymer, the second ethylene and α-olefin copolymer and the third ethylene and α-olefin copolymer each have a density differing by equal to or less than 0.002 g/cc.

25. The blend of claim 1 wherein the process capability of the blend shall be greater than about 1.33 for a dimensional tolerance of +/−1.7%.

26. A polymer blend for fabricating medical products comprising:

a first ethylene and α-olefin copolymer having a molecular weight distribution of less than about 3 and being present in an amount by weight of from about 0% to about 99% by weight of the blend and having a melt flow index from about 0.1 g/10 min to about 5 g/10 min;

a second ethylene and α-olefin copolymer having a molecular weight distribution of less than about 3 and being present in an amount by weight of the blend of from about 0% to about 99% and having a melt flow index from higher than about 5 g/10 min to about 20 g/10 min; and a third ethylene and α-olefin copolymer having a molecular weight distribution of less than about 3 and being present in an amount by weight of the blend from about 0% to about 99% and having a melt flow index greater than about 20 g/10 min.

27. The blend of claim 26 wherein the first, second and third ethylene and α-olefin copolymers have a molecular weight distribution of less than about 2.8.

28. The blend of claim 26 wherein the first, second and third ethylene and α-olefin copolymers have a molecular weight distribution of less than about 2.5.

29. The blend of claim 26 wherein the first, second and third ethylene and α-olefin copolymers are obtained using a single-site catalyst.

30. The blend of claim 26 wherein the first, second and third ethylene and α-olefin copolymers are each present in an amount within the range of from about 5% to about 70% by weight of the blend.

31. The blend of claim 26 wherein the first, second and third ethylene and α-olefin copolymers are each present in substantially equal quantities by weight of the blend.

32. The blend of claim 26 when fabricated into a monolayer tubing has a modulus of elasticity of less than about 30,000 psi.

33. The blend of claim 26 when fabricated into a monolayer tubing has a modulus of elasticity of less than about 20,000 psi.

34. The blend of claim 26 when fabricated into a monolayer tubing has a modulus of elasticity of less than about 10,000 psi.

35. The blend of claim 26 when fabricated into a monolayer tubing has an internal haze less than about 25%.

36. The blend of claim 26 is capable of being fabricated into a monolayer tubing at a throughput rate of greater than about 100 ft/min.

37. The blend of claim 26 is capable of being fabricated into a monolayer tubing at a throughput rate of greater than about 200 ft/min.

38. The blend of claim 27 is capable of being fabricated into a monolayer tubing at a throughput rate of greater than about 300 ft/min.

39. The blend of claim 26 is capable of being fabricated into a monolayer tubing at a throughput rate of greater than about 350 ft/min.

40. The blend of claim 26 when fabricated into a monolayer tubing has a substantially smooth surface.

41. The blend of claim 26 when fabricated into a monolayer tubing has less than about 10 mg of low molecular weight extractible components.

42. The blend of claim 26 when fabricated into a monolayer tubing has a yield strength within the range of from about 500 psi to about 1000 psi.

43. The blend of claim 26 when fabricated into a monolayer tubing has a yield strength of from about 600 psi to about 1000 psi.

44. The blend of claim 26 when fabricated into a monolayer tubing is capable of being used with a medical tubing clamp without significantly damaging the tubing.

45. The blend of claim 26 when fabricated into a monolayer tubing is capable of solvent bonding to a rigid component.

46. The blend of claim 45 wherein the rigid component is fabricated from a cyclic olefin containing polymer or a bridged polycyclic hydrocarbon containing polymer.

47. The blend of claim 26 wherein the first ethylene and α-olefin copolymer, the second ethylene and α-olefin copolymer and the third ethylene and α-olefin copolymer each have a refractive index with the refractive indicies differing by equal to or less than 0.08.

48. The blend of claim 26 wherein the first ethylene and α-olefin copolymer, the second ethylene and α-olefin copolymer and the third ethylene and α-olefin copolymer each have a refractive index with the refractive indicies differing by equal to or less than 0.04.

49. The blend of claim 26 wherein the first ethylene and α-olefin copolymer, the second ethylene and α-olefin copolymer and the third ethylene and α-olefin copolymer each have a refractive index with the refractive indicies differing by equal to or less than 0.01.

50. The blend of claim 26 wherein the process capability of the blend shall be greater than about 1.33 for a dimensional tolerance of +/−1.7%.

51. The blend of claim 26 wherein the first ethylene and α-olefin copolymer, the second ethylene and α-olefin copolymer and the third ethylene and α-olefin copolymer each have a density differing by equal to or less than 0.008 g/cc.

52. The blend of claim 26 wherein the first ethylene and α-olefin copolymer, the second ethylene and α-olefin copolymer and the third ethylene and α-olefin copolymer each have a density differing by equal to or less than 0.004 g/cc.

53. The blend of claim 26 wherein the first ethylene and α-olefin copolymer, the second ethylene and α-olefin copolymer and the third ethylene and α-olefin copolymer each have a density differing by equal to or less than 0.002 g/cc.

54. A medical tubing comprising:
a sidewall of a polymer blend comprising a first ethylene and α-olefin copolymer having a molecular weight distribution of less than about 3 and being present in an amount by weight of from about 0% to about 99% by weight of the blend and having a melt flow index from about 0.1 g/10 min to about 5 g/10 min, a second ethylene and α-olefin copolymer having a molecular weight distribution of less than about 3 and being present in an amount by weight of the blend of from about 0% to about 99% and having a melt flow index from higher than about 5 g/10 min to about 20 g/10 min, and a third ethylene and α-olefin copolymer having a molecular weight distribution of less than about 3 and being present in an amount by weight of the blend from about 0% to about 99% and having a melt flow index greater than about 20 g/10 min.

55. The tubing of claim 54 wherein the first, second and third ethylene and α-olefin copolymers have a molecular weight distribution of less than about 2.8.

56. The tubing of claim 54 wherein the first, second and third ethylene and α-olefin copolymers have a molecular weight distribution of less than about 2.5.

57. The tubing of claim 54 wherein the first, second and third ethylene and α-olefin copolymers are obtained using a single-site catalyst.

58. The tubing of claim 54 wherein the first, second and third ethylene and α-olefin copolymers are each present in an amount within the range of from about 5% to about 70% by weight of the blend.

59. The tubing of claim 54 wherein the first, second and third ethylene and α-olefin copolymers are each present in substantially equal quantities by weight of the blend.

60. The tubing of claim 54 having a modulus of elasticity of less than about 30,000 psi.

61. The tubing of claim 54 having a modulus of elasticity of less than about 20,000 psi.

62. The tubing of claim 54 having a modulus of elasticity of less than about 10,000 psi.

63. The tubing of claim 54 having an internal haze less than about 25%.

64. The tubing of claim 54 is capable of being fabricated at a throughput rate of greater than about 100 ft/min.

65. The tubing of claim 54 is capable of being fabricated at a throughput rate of greater than about 200 ft/min.

66. The tubing of claim 54 is capable of being fabricated at a throughput rate of greater than about 300 ft/min.

67. The tubing of claim 54 is capable of being fabricated at a throughput rate of greater than about 350 ft/min.

68. The tubing of claim 54 has a substantially smooth surface.

69. The tubing of claim 54 having less than about 10 mg of low molecular weight extractible components.

70. The tubing of claim 54 having a yield strength within the range of from about 500 psi to about 1000 psi.

71. The tubing of claim 54 having a yield strength of from about 600 psi to about 1000 psi.

72. The tubing of claim 54 is capable of being used with a medical tubing clamp without significantly damaging the tubing.

73. The tubing of claim 54 is capable of solvent bonding to a rigid component.

74. The tubing of claim 73 wherein the rigid component is fabricated from a cyclic olefin containing polymer or a bridged polycyclic hydrocarbon containing polymer.

75. The tubing of claim 54 wherein the first ethylene and α-olefin copolymer, the second ethylene and α-olefin copolymer and the third ethylene and α-olefin copolymer each have a refractive index with the refractive indicies differing by equal to or less than 0.08.

76. The tubing of claim 54 wherein the first ethylene and α-olefin copolymer, the second ethylene and α-olefin copolymer and the third ethylene and α-olefin copolymer each have a refractive index with the refractive indicies differing by equal to or less than 0.04.

77. The tubing of claim 54 wherein the first ethylene and α-olefin copolymer, the second ethylene and α-olefin copolymer and the third ethylene and α-olefin copolymer each have a refractive index with the refractive indicies differing by equal to or less than 0.01.

78. The tubing of claim 54 wherein the process capability of the tubing shall be greater than about 1.33 for a dimensional tolerance of +/−1.7%.

79. The tubing of claim 54 is a monolayer tubing.

80. The tubing of claim 54 is a multiple layered tubing wherein the blend defines a layer within the multiple layered tubing.

81. The tubing of claim 54 wherein the first ethylene and α-olefin copolymer, the second ethylene and α-olefin copolymer and the third ethylene and α-olefin copolymer each have a density differing by equal to or less than 0.008 g/cc.

82. The tubing of claim 54 wherein the first ethylene and α-olefin copolymer, the second ethylene and α-olefin copolymer and the third ethylene and α-olefin copolymer each have a density differing by equal to or less than 0.004 g/cc.

83. The tubing of claim 54 wherein the first ethylene and α-olefin copolymer, the second ethylene and α-olefin copolymer and the third ethylene and α-olefin copolymer each have a density differing by equal to or less than 0.002 g/cc.

84. A medical film comprising:
  a polymer blend comprising a first ethylene and α-olefin copolymer having a molecular weight distribution of less than about 3 and being present in an amount by weight of from about 0% to about 99% by weight of the blend and having a melt flow index from about 0.1 g/10 min to about 5 g/10 min, a second ethylene and α-olefin copolymer having a molecular weight distribution of less than about 3 and being present in an amount by weight of the blend of from about 0% to about 99% and having a melt flow index from higher than about 5 g/10 min to about 20 g/10 min, and a third ethylene and α-olefin copolymer having a molecular weight distribution of less than about 3 and being present in an amount by weight of the blend from about 0% to about 99% and having a melt flow index greater than about 20 g/10 min.

85. The film of claim 84 wherein the first, second and third ethylene and α-olefin copolymers have a molecular weight distribution of less than about 2.8.

86. The film of claim 84 wherein the first, second and third ethylene and α-olefin copolymers have a molecular weight distribution of less than about 2.5.

87. The film of claim 84 wherein the first, second and third ethylene and α-olefin copolymers are obtained using a single-site catalyst.

88. The film of claim 84 wherein the first, second and third ethylene and α-olefin copolymers are each present in an amount within the range of from about 5% to about 70% by weight of the blend.

89. The film of claim 84 wherein the first, second and third ethylene and α-olefin copolymers are each present in substantially equal quantities by weight of the blend.

90. The film of claim 84 having a modulus of elasticity of less than about 30,000 psi.

91. The film of claim 84 having an internal haze less than about 25%.

92. The film of claim 84 is capable of being fabricated at a throughput rate of greater than about 300 ft/min.

93. The film of claim 84 is capable of being fabricated at a throughput rate of greater than about 400 ft/min.

94. The film of claim 84 is capable of being fabricated at a throughput rate of greater than about 500 ft/min.

95. The film of claim 84 has a substantially smooth surface.

96. The film of claim 84 having less than about 10 mg of low molecular weight extractible components.

97. The film of claim 84 having a yield strength of from about 500 psi to about 1000 psi.

98. The film of claim 84 is capable of being solvent bonded.

99. The film of claim 84 is a monolayer film.

100. The film of claim 84 is a multiple layered film wherein the blend defines a layer within the multiple layered film.

101. The film of claim 84 wherein the first ethylene and α-olefin copolymer, the second ethylene and α-olefin copolymer and the third ethylene and α-olefin copolymer each have a refractive index with the refractive indicies differing by equal to or less than 0.08.

102. The film of claim 84 wherein the first ethylene and α-olefin copolymer, the second ethylene and α-olefin copolymer and the third ethylene and α-olefin copolymer each have a refractive index with the refractive indicies differing by equal to or less than 0.04.

103. The film of claim 84 wherein the first ethylene and α-olefin copolymer, the second ethylene and α-olefin copolymer and the third ethylene and α-olefin copolymer each have a refractive index with the refractive indicies differing by equal to or less than 0.01.

104. The film of claim 84 wherein the process capability of the film shall be greater than about 1.33 for a dimensional tolerance of +/−1.7%.

105. The film of claim 84 wherein the first ethylene and α-olefin copolymer, the second ethylene and α-olefin copolymer and the third ethylene and α-olefin copolymer each have a density differing by equal to or less than 0.008 g/cc.

106. The film of claim 84 wherein the first ethylene and α-olefin copolymer, the second ethylene and α-olefin copolymer and the third ethylene and α-olefin copolymer each have a density differing by equal to or less than 0.004 g/cc.

107. The film of claim 84 wherein the first ethylene and α-olefin copolymer, the second ethylene and α-olefin copolymer and the third ethylene and α-olefin copolymer each have a density differing by equal to or less than 0.002 g/cc.

* * * * *

UNITED STATES PATENT AND TRADEMARK OFFICE
CERTIFICATE OF CORRECTION

PATENT NO. : 6,372,848 B1
DATED : April 16, 2002
INVENTOR(S) : Tahua Yang et al.

It is certified that error appears in the above-identified patent and that said Letters Patent is hereby corrected as shown below:

Column 9,
Line 9, delete "hand" and insert -- and --

Signed and Sealed this

Seventeenth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 6,372,848 B1
DATED         : April 16, 2002
INVENTOR(S)   : Ding et al.

It is certified that error appears in the above-identified patent and that said Letters Patent is hereby corrected as shown below:

Drawings,
Sheet 2, Fig. 4, the reference numeral 20 should be applied to the peritoneal dialysis administration set; reference numeral 22 should be applied to the tubing of the peritoneal dialysis administration set; and reference numeral 24 should be applied to the container of the peritoneal dialysis set as shown on attached sheet.
Sheet 3, Fig. 7, reference numeral 50 should be applied to the medical tubing clamps; and reference numeral 54 should be applied to the slot in the medical tubing clamp as shown on attached sheet.

Column 6,
Line 19, change "52" to -- 50 --.
Line 22, change "sidewalls" to -- sidewalls 10 --.
Line 26, change "claim" to -- clamp --.

Signed and Sealed this

Twenty-seventh Day of May, 2003

JAMES E. ROGAN
*Director of the United States Patent and Trademark Office*

BLUE OUTLET PORT CLAMPS